US006187549B1

(12) United States Patent
Schmidt et al.

(10) Patent No.: US 6,187,549 B1
(45) Date of Patent: Feb. 13, 2001

(54) PROTEIN AS A DIAGNOSTIC OF CANCER

(75) Inventors: Geoffrey J. Schmidt, Norwell; Kenneth L. Hoffman, Wrentham, both of MA (US)

(73) Assignee: Cytra Corporation, Green Farms, CT (US)

( * ) Notice: Under 35 U.S.C. 154(b), the term of this patent shall be extended for 0 days.

(21) Appl. No.: 08/860,819

(22) PCT Filed: Jan. 11, 1996

(86) PCT No.: PCT/US96/00098

§ 371 Date: Dec. 18, 1997

§ 102(e) Date: Dec. 18, 1997

(87) PCT Pub. No.: WO96/21862

PCT Pub. Date: Jul. 18, 1996

(Under 37 CFR 1.47)

Related U.S. Application Data (63) Continuation-in-part of application No. 08/370,969, filed on Jan. 10, 1995, now abandoned, which is a continuation-in-part of application No. 07/858,841, filed on Mar. 27, 1992, now abandoned, which is a continuation-in-part of application No. 07/802,370, filed on Dec. 4, 1991, now abandoned, which is a continuation of application No. 07/170,737, filed on Mar. 21, 1988, now Pat. No. 5,100,661.

(51) Int. Cl.$^7$ ................................................. G01N 33/554
(52) U.S. Cl. .................. 435/7.23; 530/387.1; 530/387.7; 530/388.1; 530/388.2; 530/388.85; 530/389.1; 530/391.1; 435/7.92
(58) Field of Search .............................. 530/387.1, 387.7, 530/388.1, 388.2, 388.8, 388.85, 389.1, 389.7, 391.1, 391.3; 435/7.23, 7.92, 7.94, 7.95, 325, 330, 332, 344; 436/578, 65

(56) References Cited

U.S. PATENT DOCUMENTS

| | | |
|---|---|---|
| 4,820,631 | 4/1989 | Lacal et al. ............................... 435/6 |
| 4,870,161 | 9/1989 | Spiegel ................................. 530/326 |
| 5,100,661 | 3/1992 | Schmidt . |
| 5,405,749 | 4/1995 | Polans et al. ....................... 435/7.23 |

FOREIGN PATENT DOCUMENTS

21862 * 7/1996 (WO) .

OTHER PUBLICATIONS

Liu et al., "Incorporation of Bovine Rod Outer Segments into a Bilayer Lipid Membrane and Its transformation into a Photo–Excitable System," *Biol. Abstr.* 75(9): 7134 Ref. No. 68848 (1982).

M.J. Berridge, "The Molecular Basis of Communication within the Cell," *Scientific American*, pp. 142–152 (1983).

Schmidt et al., "Characterization of ATP–Binding Protein in Frog Rod Outer Segments," A.R.V.O. Abstracts, Mar. 1983).

Hurley et al., "Homologies Between Signal Transducing G Proteins and ras Gene Products," *Science* 27 pp. 860–860 (Nov. 1984).

R.A. Kahn et al., "Purification of a Protein Cofactor Required for ADP–ribosylation of the Stimulatory Regulatory Component of Adenylate Cyclase by Cholera Toxin," *J. Biol. Chem.* 259(10): 6228–6234 (May 25, 1984).

R.A. Kahn et al., "ADP–ribosylation of $G_8$ Promotes the Dissociation of Its α and β Subunits," *J. Biol. Chem.* 259(10): 6235–6240 (May 25, 1994).

G.J. Schmidt et al., "Further Studies on A–Protein from Rod Outer Segments," (A.R.V.O. Abstracts) Mar. 1984.

G.J. Schmidt et al., "A–Protein and G–Protein Interaction in Rods: Inhibitionof GTPASE Activity," (A.R.V.O Abstracts) Mar. 1985.

G.J. Schmidt et al., "A–Protein: Cofactor for Cholera Toxin–Dependent ADP–Ribosylation of G–Protein in Bovine ROS," (A.R.V.O Abstracts) Mar. 1986.

M.J. Berridge, "Inositol Phosphates as Second Messengers," *Phosphoinositides and Receptor Mechanisms* (Alan R. Liss, Inc., eds.) pp. 25–45 (1986).

R.A. Kahn and A.G. Gilman, "The Protein Cofactor Necessary for ADP–ribosylation of $G_s$ by Cholera Toxin is Itself a GTP Binding Protein," *J. Biol. Chem.* 261(17): 7906–7911 (Jun. 15, 1986).

R. Payne et al.,"Excitation and Adaptation of Limulus Ventral Photoreceptors by Inositol 1,4,5 Trisphosphate Result from a Rise in Intracellular Calcium," *J. Gen. Physiol.* 88(1): 127–142 (Jul. 1986).

M. Whitman et al., "Phosphoinositides, Mitogenesis, and Oncogenesis," *Phosphoinositides and Receptor Mechanisms* (Alan R. Liss, Inc. eds.) pp. 197–217 (1986).

M. Barbacid, "ras GENES" *Ann. Rev. Biochem.* 56: 779–827 (1987).

S. Cockcroft, "Polyphosphoinositide phosphodiesterase: regulation by a novel guanine nucleotide binding protein, $G_p$," *TIBS* 12–Feb., pp. 75–78 (Feb. 1987).

D.W. Corson and A. Fein, "Inositol 1,4,5–trisphosphate induces bursts of calcium release inside Limulus ventral photoreceptors," *Brain Res.* 423: 343–346 (1987).

D.A. Greene et al., "Sorbitol, Phosphoinositides, and Sodium–Potassium–ATPase In the Pathogenesis of Diabetic Complications," *N.E. J. Med.*, 316(10): 599–606 (Mar. 5, 1987).

*Primary Examiner*—Sheela Huff
(74) *Attorney, Agent, or Firm*—Hamilton, Brook, Smith & Reynolds, P.C.

(57) ABSTRACT

The presence of A-protein in an abnormally large amount in a sample, such as blood, from an individual is diagnostic of primary or metastatic cancer in the individual. The presence of A-protein is most readily detected by immunological reaction of it with specific antibodies. A preferred procedure for detecting the presence of A-protein in samples is by a sandwich assay using two antibodies with different epitopic specificities for A-protein.

34 Claims, 5 Drawing Sheets

OTHER PUBLICATIONS

R. Payne and A. Fein, "Inositol 1,4,5 Trisphophate Releases Calcium from Specialized Sites within Limulus Photoreceptors," *J. Cell Biol.* 104: 933–937 (Apr. 1987).

C.E. Thirkill et al., "Cancer–Associated Retinopathy," *Arch. Ophthalmol* 105: 372–375 (Mar. 1987).

P.J. Casey and A.G. Gilman, "G Protein Involvement in Receptor–Effector Coupling," *J. Biol. Chem.* 263(6): 2577–2580 (Feb. 25, 1988).

F.J. Rauscher III et al., "Fos–Associated Protein p39 Is the Product of the jun Proto–oncogene," *Science* 240: 1010–1016 (May 20, 1988).

J.L. Sewell and R.A. Kahn, "Sequences of the bovine and yeast ADP–ribosylation factor and comparison to other GTP–binding proteins," *Proc. Natl. Acad. Sci. USA* 85: 4620–4624 (Jul. 1988).

S.R. Price et al., "Guanine nucleotide–binding proteins that enhance choleragen ADP–ribosyltransferase activity: Nucleotide and deduced amino acid sequences of an ADP–ribosylation factor cDNA," *Proc. Natl. Acad. Sci. USA* 85: 5488–5491 (Aug. 1988).

C.E. Thirkill et al., "Cloning and Sequencing of the 23 KD Retinal CAR Antigen," *Invest. Ophthal.Vis. Sci.* 32: 935 (1991).

C.E. Thirkill et al., "The Cancer Connection: The Retinal CAR Antigen is Expressed in Small Cell Carcinoma of the Lung," *Invest. Ophthal. Vis. Sci.* 33(4): 847 (1992).

G.J. Schmidt et al., "A–Protein Catalyzes Rapid Inositol Metabolism in the Bovine Rod Outer Segment," (A.R.V.O. Abstracts, Mar., 1988).

G.J. Schmidt et al., "A–Protein is a G–Protein," (A.R.V.O. Abstracts, Mar. 1987).

R.N. Etingof et al., "Immunochemical Study of the Cyclic Nucleotide System of Retinal Photoreceptor Membranes: Antibodies Raised to Phosphodiesterase, Its Protein Inhibitor and GTP–Binding Proteins," *Brains Res.* 26(3): 415–423 (1986).

E.D. Sevier et al., "Monoclonal Antibodies in Clinical Immunology," *Clin. Chem.* 27(11): 1797–1806 (1981).

Ghose, T.I., et al. "Preparation of Antibody–Linked Cytotoxic Agents," *Methods in Enzymology* 93:280–333 (1983).

Schmidt, G.J., et al. "Activation of Membrane—Bound and Soluble A–Protein in the Bovine Rod Outer Segment," A.R.V.O. Abstracts 14, (Mar. 1989).

Schmidt, G.J., et al. "Inhibition of P1P$_2$ Hydrolysis by Monoclonal Antibodies Raised Against Bovine ROS A–Protein", A.R.V.O. Abstracts 2844–40 (1990).

Campbell, Monoclonal Antibody Technology, Elseiver Science Publishing, Chapter 1, 1986.*

* cited by examiner

SEQUENCE LISTING

<160> NUMBER OF SEQ ID NOS: 3

<210> SEQ ID NO 1
<211> LENGTH: 17
<212> TYPE: PRT
<213> ORGANISM: bovine

<400> SEQUENCE: 1

Gly Asn Ser Lys Ser Gly Ala Leu Ser Lys Glu Ile Leu Glu Glu Leu
1               5                   10                  15

-continued

```
Gln

<210> SEQ ID NO 2
<211> LENGTH: 18
<212> TYPE: PRT
<213> ORGANISM: bovine

<400> SEQUENCE: 2

Met Gly Asn Ser Lys Ser Gly Ala Leu Ser Lys Glu Ile Leu Glu Glu
1               5                   10                  15

Leu Gln

<210> SEQ ID NO 3
<211> LENGTH: 14
<212> TYPE: PRT
<213> ORGANISM: human

<400> SEQUENCE: 3

Gln Phe Glu Pro Gln Lys Val Lys Gly Lys Met Lys Asn Ala
1               5                   10
```

PROTEIN AS A DIAGNOSTIC OF CANCER

RELATED APPLICATIONS

This application is the U.S. National Phase of International Application No. PCT/US96/00098, filed on Jan. 10, 1996, which is a Continuation-In Part of U.S. Ser. No. 08/370,969, filed Jan. 10, 1995, now abandoned, which is a Continuation-in-Part of U.S. Ser. No. 07/858,841, filed Mar. 27, 1992, now abandoned, which is a Continuation-in-Part of 07/802,370, filed Dec. 4, 1991 (now abandoned), which is a Continuation of 07/170,737, filed Mar. 21, 1988 (now U.S. Pat. No. 5,100,661, issued Mar. 31, 1992), all of which are incorporated herein by reference in their entirety.

BACKGROUND OF THE INVENTION

The diagnosis of cancer in individuals has remained a difficult task to accomplish. Although some diagnostic markers are available that are assayable from blood or tissue samples, e.g. Carcinoembryonic Antigen (CEA), Alpha Fetoprotein (AFP) or Prostate Specific Antigen (PSA), the assays using these markers have not, to date, been markedly predictive of the presence of cancer in these individuals, as verified by other clinical diagnoses. The sensitivity and specificity of these assays has been disappointingly low. Time-consuming and labor-intensive clinical assessments (e.g. palpations, x-rays, mammograms, biopsies) have remained the accepted methods for diagnosing cancer. Thus, a need exists for a marker, preferably present in a biological sample, from an individual, such as blood that is predictive of the presence of cancer in the individual. In particular, a need exists for the existence of a marker and an assay to measure the presence and amount of this marker for individuals who have cancer in an early stage. If such a diagnostic test were available, early treatment with beneficial outcomes would be more likely than at present.

It is an object of this invention to provide methods for detecting the presence of primary or metastatic cancer in an individual that involves the detection of a cancer-diagnostic protein. It is also an object of this invention to provide compositions of matter that can be used to detect the presence of primary or metastatic cancer in an individual.

SUMMARY OF THE INVENTION

This invention pertains to methods of detecting cancer in an individual from the results of an assay of a biological sample, such as a blood sample, from the individual. In this assay, the sample is incubated with at least one antibody that is immunoreactive with a cancer-diagnostic protein that may be present in the biological sample. The immunoconjugates that are formed in the cancer-diagnostic protein:antibody reaction are detected. The presence of an abnormally high concentration of these immunoconjugates indicates that the individual from whom the sample was taken has primary or metastatic cancer.

In a preferred embodiment of this invention, the cancer-diagnostic protein is A-protein and the sample is incubated in a sandwich assay for A-protein. An antibody that is immunoreactive with A-protein is attached to a solid support. The sample is allowed to immunoreact with the attached antibody and with a second antibody that is immunoreactive with another region of A-protein (i.e., a region other than the region immunoreactive with the solid support-attached antibody). The resultant two antibodies-A-protein complex thereby forms a sandwich. The amount of bound second antibody is detected. This amount of detected second antibody is directly proportional to the amount of attached A-protein. An abnormally large amount of detected second antibody is indicative of the presence of primary or metastatic cancer that is being detected by the assay of the biological sample.

Another embodiment of this invention is a test kit that contains one or more antibodies to be used in the assay for the cancer-diagnostic protein (e.g. A-protein). One of the antibodies is immunoreactive with one epitopic region of the cancer-diagnostic protein and, if a second antibody is included, the second antibody is immunoreactive with an epitopic region of the cancer-diagnostic protein separate from the epitopic region that is immunoreactive with the first antibody. In a preferred embodiment of the test kit, there are two antibodies that are immunoreactive with two epitopic regions of A-protein. One of the antibodies is attached to a solid support, such as the walls and bottoms of wells of a microtiter plate. The other antibody has a detection label bound to it.

Yet another embodiment of this invention is one or more antibodies that immunoreact with a cancer-diagnostic protein, i.e. A-protein. These antibodies are used to detect or assess the presence of the cancer-diagnostic protein. The assessment can be performed using biological samples such as blood.

BRIEF DESCRIPTION OF THE DRAWINGS

FIG. 1 is a graphical representation of the chromatographic separation of soluble A-protein.

DETAILED DESCRIPTION OF THE INVENTION

The present invention pertains to methods and compositions for diagnosing the presence of primary or metastatic cancer in individuals. Primary cancer is cancerous growth that is confined to a particular anatomical region of the body or is composed of cells that formed the initial cancerous lesion. Metastatic cancer is cancerous growth that has spread from an original primary site in the body through either the blood or the lymphatic system, or both, and is growing at a site removed from the primary tumor; it is also recurrent disease spread secondary to the treatment of a primary tumor.

The primary or metastatic cancer that can be diagnosed by employing the methods and compositions of this invention are any one of a large variety of cancers. Included in this list of detectable cancers, by the methods and compositions of this invention, are breast cancer, prostate cancer, liver cancer, lung cancer, colorectal cancer, gastric tissue cancer, pancreatic cancer, bladder cancer, head and neck cancer, endometrial cancer, parotid cancer, cholangio cancer, kidney or renal cancer, cervical cancer, thyroid cancer, brain cancer, mouth cancer, uterine cancer, abdominal cancer, tongue cancer, lip cancer, anal cancer, pelvic cancer, inguinal cancer, penile cancer, chest wall cancer, fallopian tube cancer, POEMS, lymphoma, leukemia, multiple myeloma, melanoma and various sarcomas. These cancers, and most likely other types of cancer, can be detected in various stages of their progression including stage 1 and stage 2. The detection of the presence of these cancers can be distinguished from the presence of benign tumors or the absence of cancer in individuals by using the methods and compositions of this invention.

The methods of this invention preferably involve the use of antibodies that are immunoreactive with a cancer-diagnostic protein. The preferred cancer-diagnostic protein of this invention is A-protein. Following incubation of one or more of the antibodies with a biological sample from the individual, the presence of an abnormally large amount of antibody-A-protein immunoconjugate indicates the presence of primary or metastatic cancer in the individual.

Blood is an often used and preferred biological sample. When blood is the biological sample, the preferred blood constituent that is analyzed is either plasma or serum, more preferably serum. Since blood or other body fluids are preferred biological samples, the immunoreactive cancer-diagnostic protein, e.g. A-protein, is detected from a liquid medium. When blood is the biological sample, the liquid medium is circulating in the body. Thus, the methods of this invention do not rely on an analysis of localized, e.g. biopsy, material but, rather, can be employed with a readily obtainable biological sample such as blood serum or plasma. Even when such blood sampling is employed, the variety of cancers that can be detected is quite extensive.

In particular embodiments of the invention, the presence of a concentration of A-protein in a biological sample from a particular individual that is more than twice the concentration of A-protein found in similar samples from individuals without cancer is indicative of the presence of cancer in that particular individual. In other words, if biological samples of the same size are taken from individuals who are free of cancer and the average (mean) amount of A-protein in these samples is determined, an individual is predicted to have cancer if a biological sample of the same size from that individual has more than twice the amount of A-protein in it than was determined as the average amount of A-protein for the cancer-free individuals. In these particular embodiments, the factor of 2.0 is considered to be a threshold value. Individuals are predicted to have cancer if concentrations of A-protein in biological samples from them have more than 2.0 times that of the average concentration of A-protein for cancer-free individuals, i.e., if the ratio of the A-protein concentration from the tested individual's sample to the A-protein concentration average from cancer-free individuals is greater than 2.0. Ratios of tested individual's A-protein concentration to the cancer-free individuals' A-protein concentration average of less than 2.0 indicates that the tested individual does not have cancer. The threshold value of 2.0 is a particularly preferred value. Other threshold values can be established for predicting the presence of cancer in an individual. These threshold values will depend on the accuracy and reproducibility of the particular cancer diagnostic assay as well as the predictive reliability that is sought for the assay.

The actual amount or concentration of A-protein in a biological sample from an individual can have diagnostic or prognostic value. By determining the quantity of A-protein over a period of time for an individual, it is possible to monitor the progressiveness of the cancer (as the quantity of A-protein increases) or the regression of the cancer, e.g. as a result of therapeutic treatment (as the quantity of A-protein decreases). The quantity of A-protein that is detected can be meaningful as an indicator of the presence and vigor of cancer growth. The A-protein quantity is monitored in relation to a baseline value for that individual or in comparison to the average amount of A-protein in similar biological samples from cancer-free individuals. When the A-protein quantity is greater than a particular value, established by the monitor of the assay, the individual is considered to have cancer. The actual A-protein quantities in excess of this established value indicate the severity of the cancer and lesser A-protein quantities, with or without therapeutic treatments, indicate a diminution of cancer severity.

In other particular embodiments of the invention, the presence of more than about 10 ng of A-protein per ml of blood is predictive of metastatic cancer. In these methods, assays for metastatic cancer are also based on measurements of the amount of A-protein in biological samples (e.g., fluid samples such as blood plasma or serum, urine, etc.) from an individual. Again, the amount of A-protein in the biological sample is indicative of the presence or absence of metastatic cancer in the individual from whom the sample was obtained. An abnormally large amount of A-protein indicates the presence of metastatic cancer; a normal amount of A-protein indicates that the individual does not have metastatic cancer.

The usefulness of these assays is readily apparent: a relatively simple assay is predictive of the presence or absence of primary or metastatic cancer.

A variety of techniques are known and available to the artisan for assaying for the amount of A-protein in a biological sample. These techniques include isolating and quantifying the A-protein in the sample by solvation and centrifugation procedures, by column chromatography or gel electrophoretic separation procedures, by filtration procedures, by enzymatic recognition procedures, or by binding procedures with molecules that recognize and bind A-protein with specificity such as affinity chromatography or immunoassay. Such specific binding processes can also be used to detect and quantify the A-protein in situ in biological samples by assessing the volume or area distribution of the specific binding molecule in the sample.

A preferable technique for assaying for the amount of A-protein in a biological sample is immunological recognition with antibodies that specifically bind A-protein or particular epitopes of A-protein. Such antibodies are compositions of the present invention. These antibodies selectively recognize A-protein determinants and bind to these determinants with high affinity. The antibodies can be used singly as affinity immobilization or as tagging binding moieties in procedures such as Western blot or electrophoretic pattern analyses, or multiply to bind to different A-protein determinants or epitopes such as in sandwich assays. These antibodies can have substances that act as labels attached to them for ease of identification following binding of the antibody to A-protein. The antibodies of this invention bind to A-protein with specificity so A-protein or specific epitopes of A-protein can be detected with particularity.

Antibodies which can be used within this invention are reactive with A-protein. The term antibody is also intended to encompass both polyclonal and monoclonal antibodies. The term antibody is intended to encompass mixtures of more than one antibody reactive with A-protein (e.g., a cocktail of different types of monoclonal antibodies reactive with A-protein). The term antibody is further intended to encompass whole antibodies, biologically functional fragments thereof, single chains or single chain fragments with A-protein binding properties, and chimeric antibodies comprising portions from more than one species, bifunctional antibodies, etc. Biologically functional antibody fragments which can be used are those fragments sufficient for binding of the antibody fragment to A-protein.

The chimeric antibodies can comprise portions derived from two different species (e.g., human constant region and murine variable or binding region). The portions derived from two different species can be joined together chemically by conventional techniques or can be prepared as fusion proteins using genetic engineering techniques. In addition, DNA encoding the proteins of both the light chain and heavy chain portions of the chimeric antibody can be expressed together as fusion proteins.

It has been determined that particular intracellular molecules, called A-proteins, are intimately involved in the regulation of the inositol-related signal transducing system. In this system, A-proteins function by activating phospholipase C (PL-C) to generate the second messengers inositol-1,4,5-trisphosphate ($IP_3$) and diacylglycerol (DG). Upon stimulation of a membrane bound receptor, an A-protein binds with GTP to form an intermediate which functions to activate PL-C. When the GTP of the intermediate is hydrolyzed to GDP, PL-C activation terminates. A-proteins are accordingly important G-type signal transducing molecules critical to proper functioning of the cellular inositol metabolic pathway.

These signal transducing molecules are useful in producing the antibodies that are used in the foregoing methods of the present invention. The signal transducing molecules that are used to produce the antibodies are isolated and purified A-proteins and epitopic fragments of A-protein.

The cancer-diagnostic proteins of the invention, e.g. A-protein, can also be useful in immunotherapy. When these proteins are introduced into the blood or lymphatic system, they can stimulate the immune system to respond, i.e. to recognize the presence of cancer in the host and to respond to it. Thus, by introducing these cancer-diagnostic proteins into the individual's bloodstream or lymphatic system from external sources, the immune system can be stimulated to generate immunosuppressive activity to eradicate the cancer.

In addition, the antibodies of this invention can have therapeutic value. When they are administered to an individual, they can immunoreact with the cancer-diagnostic protein, e.g. A-protein, and thereby initiate further immune system response, e.g. by stimulating the production of T-cells, to eliminate the cancer cells present in the individual.

The term "A-protein" was originally used to describe a rod photoreceptor protein of approximately 20 kilodaltons molecular weight based on the electrophoretic mobility of this protein through a gel under reducing conditions. From, an analysis of the protein as an expressed product of the known A-protein gene, the molecular weight of the A-protein is 26 kilodaltons. Improved extraction and separation methods combined with preliminary sequence data on the separated forms indicates that the entity referred to previously as A-protein may consist of at least two structurally and functionally related proteins; one membrane-bound and one soluble. On this basis, the terminology used reflects the presumed in vivo state: $A_m$, membrane bound (20 kD); and $A_s$, soluble (19 kD), again based on electrophoretic mobility under reducing conditions. These A-proteins include the amino acid sequences for the N-terminal regions set forth in the Sequence Listing as:

GNSKSGALSKEILEELQ (SEQ ID NO:1) ($A_m$); and
MGNSKSGALSKEILEELQ (SEQ ID NO:2) ($A_s$).

Further characterizations of the A-protein related molecules are that they comprise a single polypeptide chain with a significantly hydrophobic region. These molecules also have the ability to bind and hydrolyze the nucleotides adenosine and guanosine triphosphate, and have the ability to activate phospholipase C, phospholipase D, and possibly also phospholipase $A_2$, in the presence of GTP.

A-proteins can be isolated from mammalian (bovine) and amphibian (frog) rod outer segments (ROS) of photoreceptor cells of the eye by extraction, centrifugation, chromatography and other protein purification techniques known to those skilled in the art. Other proteins with similar or identical physical and functional characteristics as the A-proteins have been isolated from various other tissues from vertebrates and invertebrates. These findings indicate that the structure of the A-proteins has been conserved through evolution. A-proteins are quite labile in aqueous solution, but can be significantly stabilized if disposed in aqueous solutions containing a nonionic surfactant. They have a molecular weight in the range of 19 to 20 kD, as inferred by comparison to molecular weight standards during electrophoretic separations under reducing conditions. Preferred methods of isolating the native protein are disclosed in detail below. Good purification results have been achieved using filters with molecular weight cutoffs in the range of 10 kD and 30 kD.

A-proteins, various truncated or mutein analogs thereof, and fused proteins comprising an A-protein and other protein domains can be produced by various synthetic and biosynthetic means. For example, an appropriate host cell such as a microorganism, yeast, or eucaryotic cell culture can be genetically engineered to express an A-protein, or a portion or analog thereof. This may be accomplished by now well-established recombinant DNA technologies known to those skilled in the art. The recombinant procedure may include the isolation or synthesis of the gene encoding an A-protein, a portion, or analog thereof, and the integration of that gene into a plasmid. The amino acid sequences of the A-proteins may be established readily. The Sequence Listing sets forth the N-terminus amino acid sequence of two forms of A-protein ($A_m$ and $A_s$) as SEQ ID NO:1 and SEQ ID NO:2, respectively. Gene synthesis from synthetic oligonucleotides and known mutagenesis techniques provide the technologies to prepare an array of analogs, truncated A-protein forms, and fused proteins comprising A-protein or an antibody binding domain thereof. Production of such materials further may include the transformation of an appropriate host cell with a vector harboring the recombinant DNA that includes the gene encoding A-protein or a portion or analog thereof, culturing that transformed host cell, and isolation of the expressed protein. Given the availability of A-protein-rich samples producible as disclosed herein, the recombinant production of the native form and various portions and analogs thereof is well within the current skill in the art.

Alternatively, at least portions of the protein can be produced synthetically by chemically joining amino acids in the correct sequence.

The isolated A-proteins, or portion or analog thereof, can be used as antigens to produce antibodies that are useful to detect A-protein in fluid samples from individuals, thereby assaying for the presence of primary or metastatic cancer. The antibodies can be part of a polyclonal antisera, or the binding portions thereof of these antibodies, raised against A-protein, and shown to react with A-protein or with its analogs, fragments or to a particular epitope on $A_m$ or $A_s$. The antibodies can be polyclonal or monoclonal antibodies produced by methods known per se. The antibodies preferably are selected so as not to cross-react with other cellular components. The antibodies can be of any class and subclass as determined by the Ouchterlony double diffusion test. Antibodies of the IgG class are preferred. Alternatively, antibodies which recognize A-protein can be synthesized by biosynthetic or recombinant means, either in whole or in part.

In addition, the antibodies can be linked to other functional molecules such as toxins, fluorescent or absorption dyes, enzymes, or radioactive markers. In preferred embodiments, the antibodies are linked to biotin molecules which have a particularly strong avidity for avidin or streptavidin which, in turn, can be linked to fluorescent, absorption or radioactive markers. The linked antibodies can be used to detect A-protein from biological samples and thereby assay for primary or metastatic cancer. The antibody-marker complex can be prepared by chemical linkage or by recombinant DNA techniques if the marker is proteinaceous.

The antibodies can also be labelled with a reagent which enables the monitoring or imaging of the antibody immediately after its administration to a patient. The label can be, for example, a radioisotope such as $^{125}I$ or $^{99m}Tc$, both of which can be imaged extracorporeally by radiation detection means such as a gamma scintillation camera. Alternatively, the antibody can be labelled with a non-radioactive, paramagnetic contrast agent capable of detection in MRI systems. In such systems, a strong magnetic field is used to align the nuclear spin vectors of the atoms in a patient's body. The field is then disturbed and an image of the patient is read as the nuclei return to their equilibrium alignments. In the present invention, antibodies can be linked to paramagnetic materials such as gadolinium, cobalt, nickel, manganese or iron complexes, to form conjugate diagnostic contrast reagents that are imaged extracorporeally with an MRI system.

If the antibodies are not linked to functional markers, conjugates of antibody-A-protein can still be detected by using standard biochemical techniques to recover immunoprecipitates, such as centrifugation.

Anti-A-protein monoclonal antibodies can be obtained from hybridoma cell lines formed upon the fusion of mouse yeloma cells with spleen cells of mice previously immunized with A-protein that has been purified, for example, from bovine ROS. The immunogen alternatively can be a derivative of A-protein, or an analog or portion thereof, produced in vitro according to known mechanical or manual procedures of peptide synthesis. Alternatively, the immunogen (A-protein) can be synthesized by biosynthetic means using recombinant DNA technologies known to those skilled in the art. The mice whose spleen cells are chosen for fusion are preferably from a genetically defined lineage such as Balb/C. The myeloma cells used in the fusion are from a mammalian, antibody-producing cell line, but most preferably are from a mouse cell line such as, e.g., NS-1. The monoclonal antibodies can be obtained from ascites fluid of mice injected with the fusion product.

In preferred embodiments of the invention, an immunogen for the production of polyclonal or monoclonal antibodies is a peptide with an amino acid sequence of approximately 16 amino acids taken from the known amino acid sequence of A-protein. This immunogen is a peptide of 10–18 amino acids in length. In particularly preferred embodiments, the immunogen is either the 14 amino acid or 16 amino acid carboxyl terminus of A-protein, the peptide containing amino acids 60–71 of A-protein, the peptide containing amino acids 142 to 158 of A-protein or the peptide containing amino acids 158–170 of A-protein. When this immunogen is used to produce antibodies for incorporation in a sandwich assay, a second immunogen from A-protein is chosen other than the approximately 16 amino acid peptide of the first immunogen. Another technique for obtaining antibodies that immunoreact with the second immunogen of A-protein is to immunize an animal with intact A-protein and select antibodies that immunoreact with an epitope of A-protein other than that of the first immunogen. The production of two sets of antibodies with the properties of immunoreacting with different epitopes ensures that sandwich assays using these antibodies will not be impeded by competition of the antibodies for the same antigenic site. This feature increases the sensitivity of the assay for detecting the actual amount of A-protein present in the sample.

The polyclonal or monoclonal antibodies so produced by known procedures are specific for A-protein, and therefore are particularly useful for assaying for A-proteins.

In the present invention, either intact A-proteins or detectable fragments of A-proteins can be assayed by the disclosed methods. The essential feature of the intact protein or detectable fragment thereof is the ability of these proteins or peptides to be detectable, i.e. to immunoreact with immobilization or detection antibodies. Formation of the protein or fragment complexes with the antibodies and detection of these complexes are all that is required. Such detectable complexes can be formed with A-protein fragments.

This invention includes a particular method for detecting the amount of A-protein in a biological sample such as blood serum or plasma. In this method a first antibody which binds to a first epitope on A-protein is adhered to a solid support. The adhered first antibody is contacted with the biological sample to be tested. Either simultaneously or sequentially thereafter, a labeled second antibody which binds a second epitope on A-protein is added to the first antibody-biological sample mixture, thereby forming a first antibody:A-protein:second antibody immunocomplex attached to the solid support. This second antibody is attached to a detectable marker. Any unbound second antibody is removed, and the presence and, if desired, the amount of the marker is then detected, its presence and amount being indicative of the presence and the amount of A-protein in the sample. An abnormally large amount of detected A-protein, by such an assay, indicates that the individual from whom the biological sample was obtained has a high probability of having primary or metastatic cancer. In other words, this assay is diagnostic for primary or metastatic cancer.

Test kits are also embodiments of this invention. These test kits contain one or more of the polyclonal or monoclonal antibodies that are needed to perform assays for the cancer-diagnostic protein, e.g. A-protein, that may be present in the biological samples, such as blood, obtained from individuals. These test kits can also contain the solid supports, such as microtiter trays, for performing the assays. Instructions for performing the assays for A-protein can also be included in the kits. If desired, an identification label can be attached to an antibody of the test kits. In preferred embodiments of the test kits, antibodies are provided that allow sandwich assays to be performed where the antigen is A-protein. In particularly preferred embodiments of the invention, one of the sandwich antibodies is unlabeled and adhered to a solid support. The other antibody has a label bound to it for detection purposes.

The following examples further disclose the nature of the invention, without limiting the scope thereof.

EXAMPLE 1
Purification of Soluble ($A_s$) and Membrane-Bound ($A_m$) A-Protein A-proteins were isolated from the retinas of cow eyes essentially as described by Schmidt et al. (*J. Biol. Chem*, 262:14333–14336 (1987)). Bovine (cow or calf) eyes were obtained from a local abattoir within 2 hours of killing. Bovine eyes were kept on ice in the dark for 30 to 60 minutes. Retinas were dissected out and placed in buffer A (130 mM NaCl, 20 mM Tris-HCl, pH 7.0; 1 ml per calf retina or 2 ml per cow retina). Gentle, repeated inversions of the container liberated large numbers of ROS into the buffer. The mixture was poured through a Buchler funnel to remove the retinas. The filtrate was allowed to settle in a conical-bottomed tube on ice for 5 minutes, allowing gross particulate matter to settle out of the ROS suspension. The supernatant was found, by means of microscopic examination on a hemocytometer, to consist of greater than 95% ROS. The ROS were disrupted with shear which was created by repeatedly drawing the suspension into the syringe and forcing it out against the wall of the container.

To separate particulate and aqueous fractions, the suspension was centrifuged at 10,000 to 12,000×g for 20 minutes at 4° C. The pellet containing ROS membranes was washed once with a volume of buffer A equal to that of the removed supernatant. The resulting pellet was resuspended in 3 to 6 ml of buffer T ((0.05%) Tween 20/80 (1:1) in double-distilled water) and spun at 15,000×g for 45 minutes. The above manipulations were carried out under dim red light. Both A-protein solutions (the supernatants containing soluble and membrane-bound A-protein, respectively) were filtered through Centricon 30 microconcentrators (molecular weight cut-off of 30 kD, Amicon Corporation), with centrifugation at 5,000×g in a refrigerated centrifuge. The ultrafiltrates were then concentrated and dialyzed in Centricon 10's (molecular weight cut-off of 10 kD) at 5,000×g.

The retentates contained proteins of 10 kD to 30 kD, with average concentrations of 100 to 200 μg/ml for soluble A-protein ($A_s$) and 30 to 100 μg/ml for membrane-bound ($A_m$), reduced to a volume of 0.5 to 1 ml. The purification of $A_s$ resulted in a 320-fold enrichment and $A_m$ was purified 20-fold. If the soluble A-protein solution was to be kept overnight before concentration and use, buffer A with 0.05% Tween 20/80 (1:1) was added 1:5 to minimize aggregation of proteins in the concentrated solution.

The A-proteins, purified by ultrafiltration as described above were further purified for sequence analysis by HPLC on a Bio-Sil SEC-125 column in buffer A ($A_s$) or buffer T ($A_m$). Elution was isocratic. Pooled peaks were concentrated, dialyzed against water and lyophilized prior to analysis.

Figure 1A:
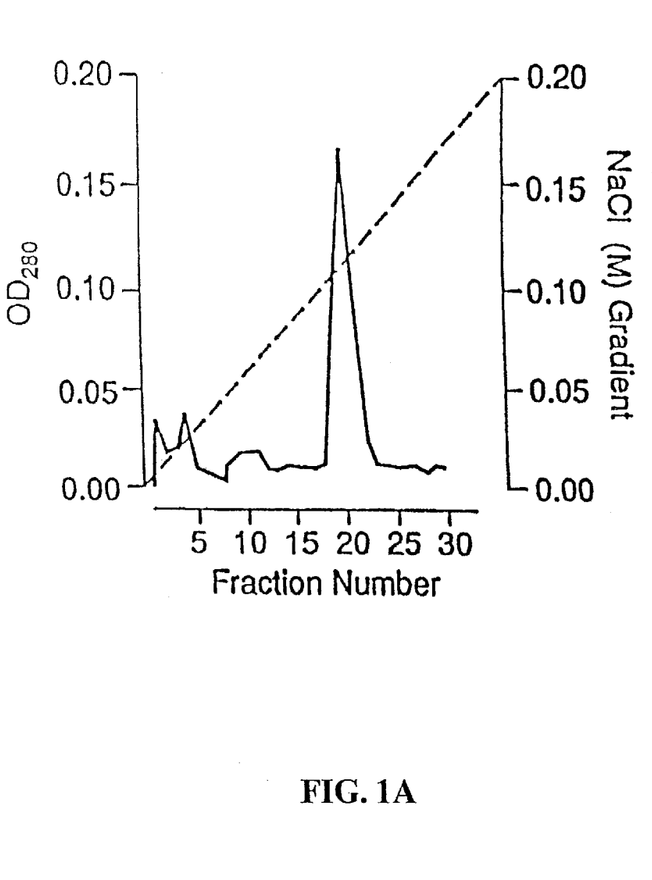
FIG. 1A is an optical scan of the $A_s$ form of A-protein purified on a high pressure liquid chromatography (HPLC) gel filtration column.
Figure 1B:
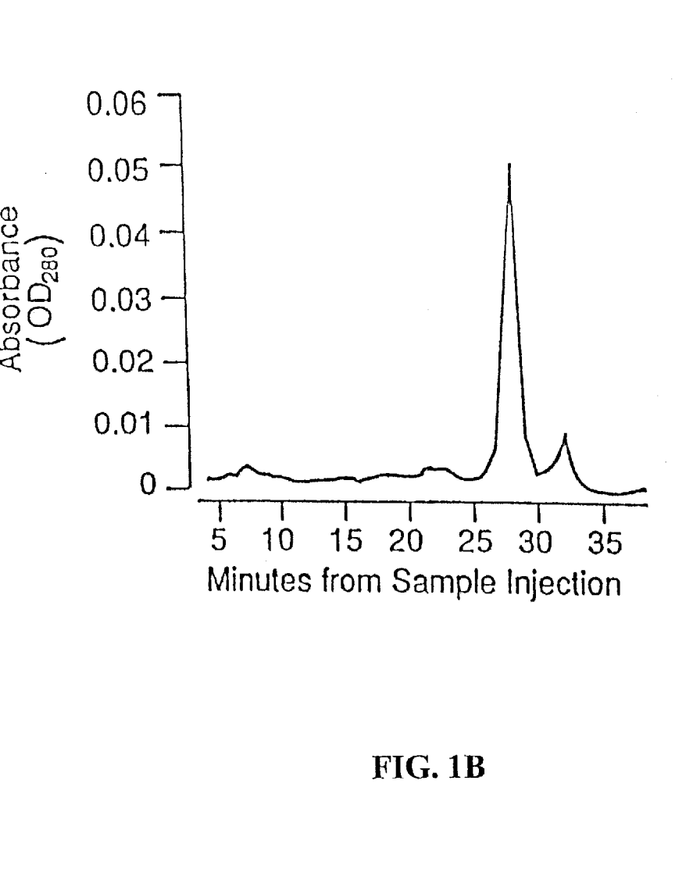
FIG. 1B is an optical scan of the HPLC-purified $A_s$ rechromatographed on a DEAE-cellulose anion exchange column with a linear salt gradient (dashed line) to confirm the effectiveness of the purification procedure.

For the purpose of confirming the purity of soluble A-protein used in experiments, $A_s$, purified by ultrafiltration as described, was run on a HPLC size exclusion column (TSK-2000, Bio-Rad) in buffer A (FIG. 1A), and then rechromatographed in 0.1 M potassium phosphate buffer on a DEAE anion-exchange column. Protein was eluted with a 0 to 200 mM NaCl gradient (FIG. 1B).

The estimation of molecular weights of $A_m$ and $A_s$ were made from the relative mobility of each on SDS gels (see Example 2 and FIG. 2) and a calibrated gel filtration column. The agreement of weight determination between the native forms from the column and the denatured forms on gels indicates that A-protein exists in vivo as a monomer.

The purification of $A_s$ as described above results in preparations of greater than 95% purity. Any protein contaminant of the purified AS preparations has been shown not to interact with guanosine or adenosine nucleotides under any of the conditions tested. Since the extractions are sequential, $A_m$ is purified to essential homogeneity by the procedure described with no detectable contaminants, as shown in the SDS gel described below in Example 2 and pictured in FIG. 2, lane 1.

Once purified, the stability of the A-proteins differs markedly in aqueous solution. $A_m$ is metastable in the purified state and retains most of its functional properties for several days at 4° C. $A_m$ can also withstand freezing and thawing in detergent without losing more than 15 to 20% of its original activity. In contrast, $A_s$ is labile under a variety of conditions and no satisfactory methods of treatment have been found to prevent greater than 80% activity loss over a 48 hour period of 4° C. The soluble A-protein is markedly thermo- and cryolabile. Purified $A_s$ loses activity rapidly at room temperature (half life=2 hrs) and freezing results in loss of virtually all activity, presumably due to denaturation and/or aggregation. The purified soluble form aggregates readily in the absence of detergent treatment and will precipitate overnight in the refrigerator under those conditions.

EXAMPLE 2
Gel Electrophoresis of Soluble ($A_s$) and Membrane-Bound ($A_m$) A-Protein Polyacrylamide gel electrophoresis was performed according to a modification of the methods of O'Farrell (*J. Biol. Chem.*, 250:4007 (1975)) in the presence of 0.1% SDS in a pore gradient gel (10 to 20%). Samples were applied in a sample buffer of 0.33 mM DTT, 7% SDS, 17% glycerol and 0.5 M Tris-HCl, pH 6.8, and run to equilibrium. Samples were not heat-denatured, in order to avoid the appearance of additional bands caused by the formation of stable polymers. Proteins were visualized with the Bio-Rad silver stain kit. Gels were calibrated using pre-stained molecular weight standards from Bio-Rad (range 17 to 94 kD).

Figure 2:
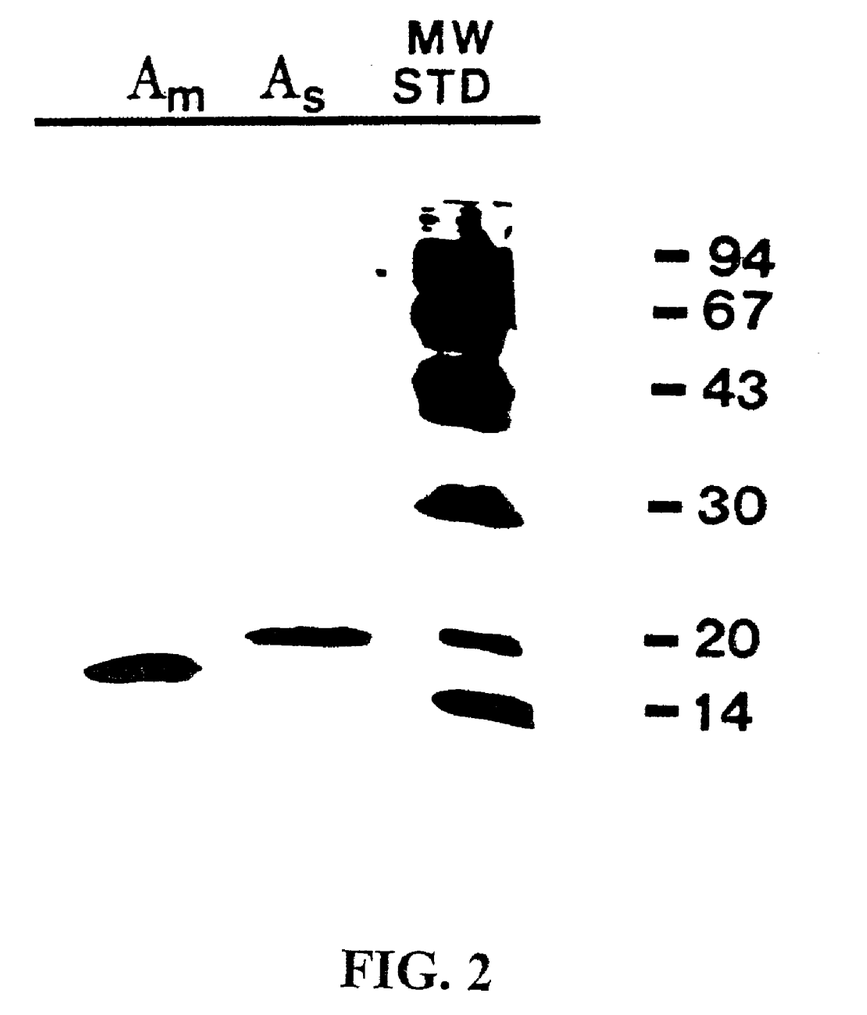
FIG. 2 is a photographic representation of the purification of the $A_m$ and $A_s$ forms of the A-protein by SDS-PAGE. The gel was stained with silver. Lane 1 is purified $A_m$; lane 2 is purified $A_s$; lane 3 shows molecular weight standards.

As shown in FIG. 2, "A-protein" includes $A_m$, a membrane bound form having a molecular weight of about 20 kD and $A_s$, a soluble form having a molecular weight of about 19 kD when the gels are run under reducing conditions. The soluble protein resolves into two closely spaced bands on gels. The membrane-bound form migrates as a single band.

EXAMPLE 3
Production of Murine Polyclonal and Monoclonal Antibodies to A-Protein Balb/c mice (6–8 weeks old; The Jackson Laboratory, Bar Harbor, Me.) were immunized with four injections of A-protein. The injections were performed one week apart and 50 μg A-protein (either $A_s$, $A_m$, or both) was injected on each occasion. The first three injections were given intraperitoneally, and the fourth intravenously. A-protein was injected with complete Freunds adjuvant on the first occasion, incomplete adjuvant on the second and third occasions, and without adjuvant on the last occasion. Serum withdrawn prior to the last injection showed prominent binding to purified A-protein using a solid phase microtiter plate enzyme-linked immunoassay. The mouse with the best immune response was sacrificed three days after the last injection. Lymphocytes from this animal were maintained as a polyclonal hybridoma by subcloning them as antibody producer cells in a Cellco bioreactor. These producer cells were maintained in liquid nitrogen cryostorage. The murine polyclonal antibodies from these producer cells displayed specificity for A-protein.

Monoclonal hybridomas were produced by fusion of spleen cells from the sacrificed mouse with NS-1 (P3NS-1/1-Ag4-1) myeloma cells (American Type Culture Collection, Rockville, Md.; Accession No. TIB18). The method of Nadakavukaren (*Differentiation*, 27:209–212, (1984)) was employed to perform the fusions. Resultant clones were tested for binding to A-protein. Subcloning by serial dilution was carried out on one clone. The most productive subclones were injected into the peritoneal cavity of Balb/c mice to produce ascites fluid containing monoclonal antibody. The ascites fluid which was obtained was centrifuged, tested for activity, and then stored at −70° C. until required.

The resulting 18 anti-A-protein antibodies were screened for antibody isotype by the Ouchterlony double diffusion test in agar plates against anti-IgM, anti-IgG, anti-IgG1, anti-IgG2a, anti-IgG2b, and anti-IgG3 antibodies (Cappell). The results are shown in TABLE 1.

TABLE 1

| mAb name | isotype | mAb name | isotype |
| --- | --- | --- | --- |
| 3A9A5 | IgG 2a | 3A9F2 | IgG 2a |
| 3A12D7 | IgM | 3A12E9 | IgM |
| 4C5B4 | IgM | 4C5F3 | IgM |
| 5E6B1 | n.d. | 5E6H5 | n.d. |
| 7E4F9 | n.d. | 7E4H12 | n.d. |
| 9D8F8 | IgG 2a | 9D8G11 | IgG 2a |
| 1B9B2 | IgG 1 | 3A7G6 | n.d. |
| 3B6C12 | IgG 2a | 3B9E1 | IgM, IgG (mixed expression) |
| 3F5H11 | n.d. | 4C8B2 | n.d. |

"n.d."—not determined

EXAMPLE 4
Assays for GTP and ATP Binding and Hydrolysis by A-Protein; Protein Amount; and A-Protein Presence A. GTPase and ATPase Assays The rate of hydrolysis of GTP or ATP by both soluble and membrane-bound A-protein was assayed in a total volume of 200 μl. 1.0 to 10.0 μg $A_s$ or $A_m$, $5 \times 10^{-5}$ M GTP or ATP, 67 to 335 nM [γ-$^{32}$P] GTP (2.8 Ci/mmol) or 88.8 to 177.5 nM [γ-$^{32}$P] ATP (2.8 Ci/mmol) and 20 μl of stripped ROS membranes (in the case of $A_m$) were mixed in buffer J (20 mM Tris-HCl, pH 7.0, 0.1 mM EDTA). The stripped ROS membranes (containing rhodopsin as the receptor) were prepared by washing ROS membranes 3 times in buffer C (100 mM NaCl, 20 mM Tris-HCl, pH 7.0, 1 mM MgCl$_2$) and 3 times in water containing 0.01% polyoxyethylene 23 lauryl ether (Brij 35 nonionic detergent, Sigma Chemical Co.). The stripped membranes were resuspended in buffer D (10 mM Tris-HCl, pH 7.0, 0.1 mM EGTA) prior to use.

The effect of light on the hydrolysis of GTP or ATP was investigated by means of duplicate incubations in light exposure trials (a bright 10 msec xenon flash (Nikon) delivering $1.8 \times 10^3$ μWcm$^{-2}$sec$^{-1}$ which was sufficient to bleach greater than 70% of the rhodopsin present in each sample) or kept in the dark as controls. Samples were incubated at room temperature for 5 minutes and quenched with 200 μl ice-cold quench buffer (50 nM KH$_2$PO$_4$, 6% Norite A, 10% TCA). The samples were kept on ice for 30 minutes and spun down for 5 minutes in a microcentrifuge. 50 μl aliquots of each supernatant were placed in a vial with 5 ml scintillation fluid and assayed for radioactivity. The hydrolysis of [γ-$^{32}$P]-GTP was measured in the presence and absence of photolyzed rhodopsin.

The GTPase activity of $A_m$ was enhanced in the presence of the activated receptor. In contrast, no effect on the hydrolysis rate was observed when unphotolyzed rhodopsin was added to the incubation in the dark. In the absence of rhodopsin or the presence of unbleached rhodopsin, $A_m$ had negligible GTPase activity.

On a mol/mol basis, the rate of GTP hydrolysis by $A_m$ (0.458 GTP sec$^{-1}$/$A_m$) is comparable to that of transducin (0.512 GTP sec$^{-1}$/Tα) when both are measured at submaximal velocity in the presence of photoactivated rhodopsin. The GTPase rates for $A_m$ and transducin are additive when the two purified proteins are present in approximately equimolar concentrations.

Under all experimental conditions tested, the rate of GTP hydrolysis (GTPase activity) by purified $A_s$ was insensitive to the presence of bleached or unbleached rhodopsin.

The apparent Michaelis constant was determined for $A_s$ and $A_m$ by measuring the rate of GTP hydrolysis over a thousand-fold range of substrate concentrations. $K_m$ and $V_{max}$ were determined by construction of double reciprocal plots and regression analysis. Data are presented as mean±S.D. The results are given in TABLE 2.

TABLE 2

| Values For | GTPase | (n) | ATPase | (n) |
| --- | --- | --- | --- | --- |
| $K_m$:$A_S$ | $2.06 \pm 2.46 \times 10^{-6}$M | (4) | $1.50 \pm 1.47 \times 10^{-4}$M | (3) |
| $K_m$:$A_m$ | $2.39 \pm 1.87 \times 10^{-6}$M | (3) | $1.44 \pm 0.56 \times 10^{-5}$M | (3) |
| $V_{max}$:$A_S$ | N.D. | | 0.56 (±0.09) pmol/mg A-protein min$^{-1}$ | |
| $V_{max}$:$A_m$ | 16.4 nmol/mg$A_m$min$^{-1}$ | | 2.90 (±0.16) pmol/mg A-protein min$^{-1}$ | |

In the presence of rhodopsin the $K_m$ values for $A_m$ and $A_s$ are similar indicating similar affinities for GTP.

$A_m$ and $A_s$ were found to have ATPase activity that was not receptor coupled. The $K_m$ values for both $A_m$ and $A_s$ ATPases are given in TABLE 2, above. Comparison of the rate constants of $A_m$ indicates that its affinity for ATP is approximately an order of magnitude greater than that of $A_s$. The relative $K_m$ values for GTPase and ATPase activity of both $A_m$ and $A_s$ indicate that GTP is the preferred substrate for binding and hydrolysis.

The addition of rhodopsin to incubations did not enhance the rate of ATP hydrolysis of either protein. The ATPase rate declines slightly in the presence of the activated receptor.

B. GTP Binding Assays

Assays of the binding of the GTP-analogs Gpp(NH)p and GTPγS (New England Nuclear) by both $A_m$ and $A_s$ were performed according to the methods of Northup et al. (*J. Biol. Chem.*, 257:11416–11423 (1982)). Binding was carried out in a total volume of 100 μl of solution containing 5 to 10 μg purified A-protein, 15.3 μM $^3$H-Gpp(NH)p (10 μCi) or 1.32 μM GTPγS$^{35}$ (1 μCi) and buffer (100 mM NaCl, 0.1 mM EDTA, 20 mM Tris-HCl, pH 7.0). The samples were vortexed and incubated at 25° C. for 30 minutes, quenched with 200 μl ice-cold buffer (0.5 M NaCl, 0.1 M Tris-HCl, 0.1% Tween 80), and kept on ice for 30 minutes. The samples were placed onto nitrocellulose filters that had been previously washed with 2 ml of the same buffer. The filters were rinsed 5 times with 2 ml ice-cold buffer and assayed for radioactivity.

$A_m$ bound both GTPγS and Gpp(NH)p spontaneously during a brief incubation at room temperature. The results are shown in TABLE 3 below.

TABLE 3

| Form of A-protein | Gpp(NH)p mol GTP | GTPγS Analog/mol Protein |
|---|---|---|
| $A_m$ | 0.57 ± 0.12 | 0.93 |
| $A_s$ | 0.29 ± 0.08 | 0.47 |

This process apparently required no cofactors. $A_m$ bound less than stoichiometric amounts from each GTP analog under the experimental conditions used (TABLE 3). $A_s$ bound significantly less of these analogues on a mol/mol basis after a similar incubation in the absence of cofactors. GTPγS was more readily bound than Gpp(NH)p by both $A_m$ and $A_s$.

C. ATP/GTP Competition

Figure 3:
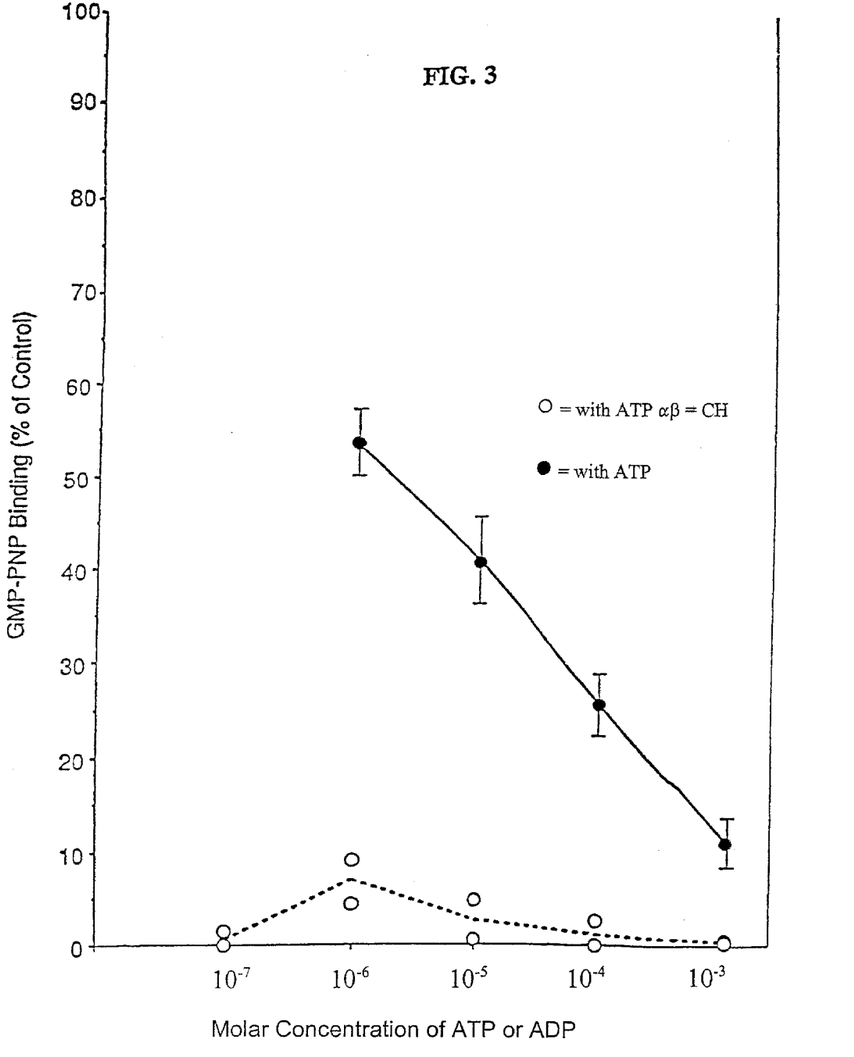
FIG. 3 is a graphic representation of the binding of the GTP-analog GMP-PNP by soluble and membrane-bound forms of A-protein in the presence of adenosine nucleotides.

The effect of adenosine nucleotides on the binding of Gpp(NH)p to a mixture of $A_m$ and $A_s$ was examined because of the ability of the A-proteins to bind and hydrolyze ATP. Purified $A_m$ and $A_s$ were mixed (1:2), preincubated with ATP or ADP, and assayed for Gpp(NH)p binding after a brief incubation by the rapid filtration method. As shown in FIG. 3, ATP was an effective inhibitor of binding at all concentrations tested. ADP was inhibitory in a concentration-dependent manner at higher concentrations.

Figure 4:
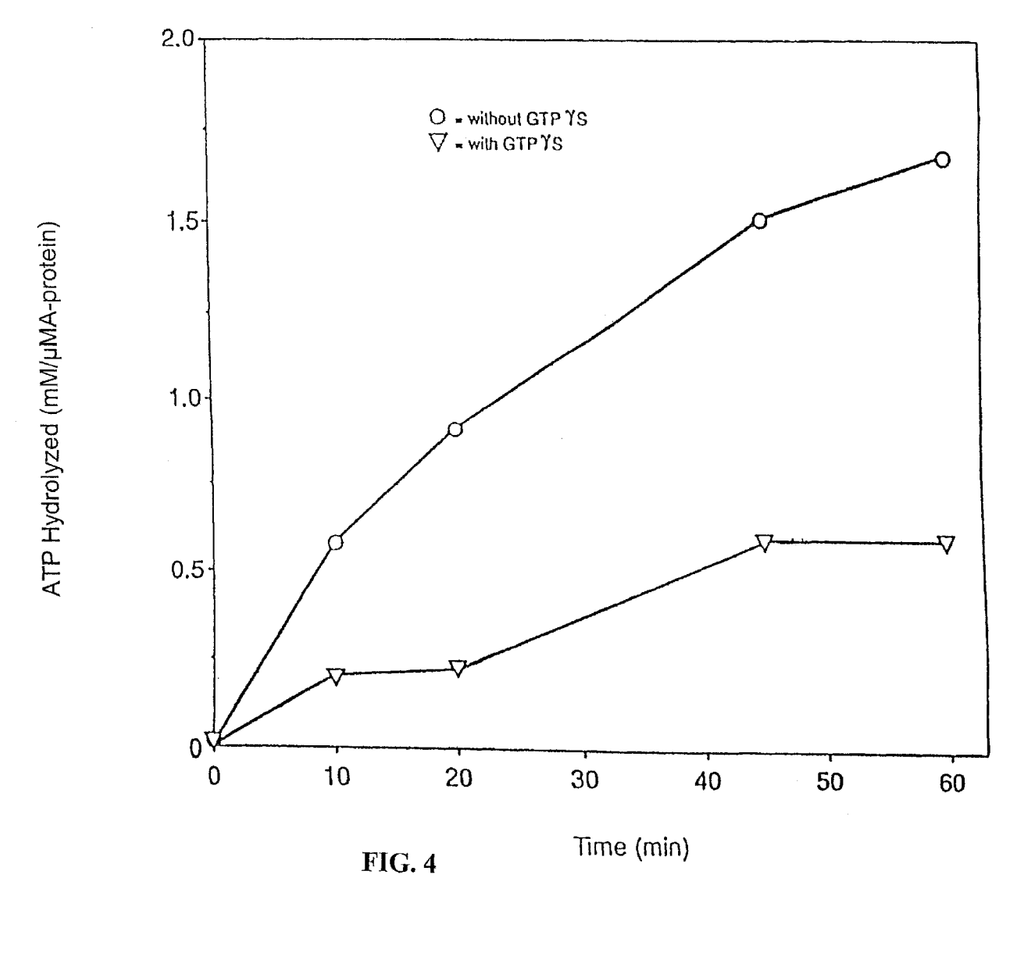
FIG. 4 is a graphic representation of the ATPase activity of $A_s$ and $A_m$ in the presence of GTPγS.
Figure 5:
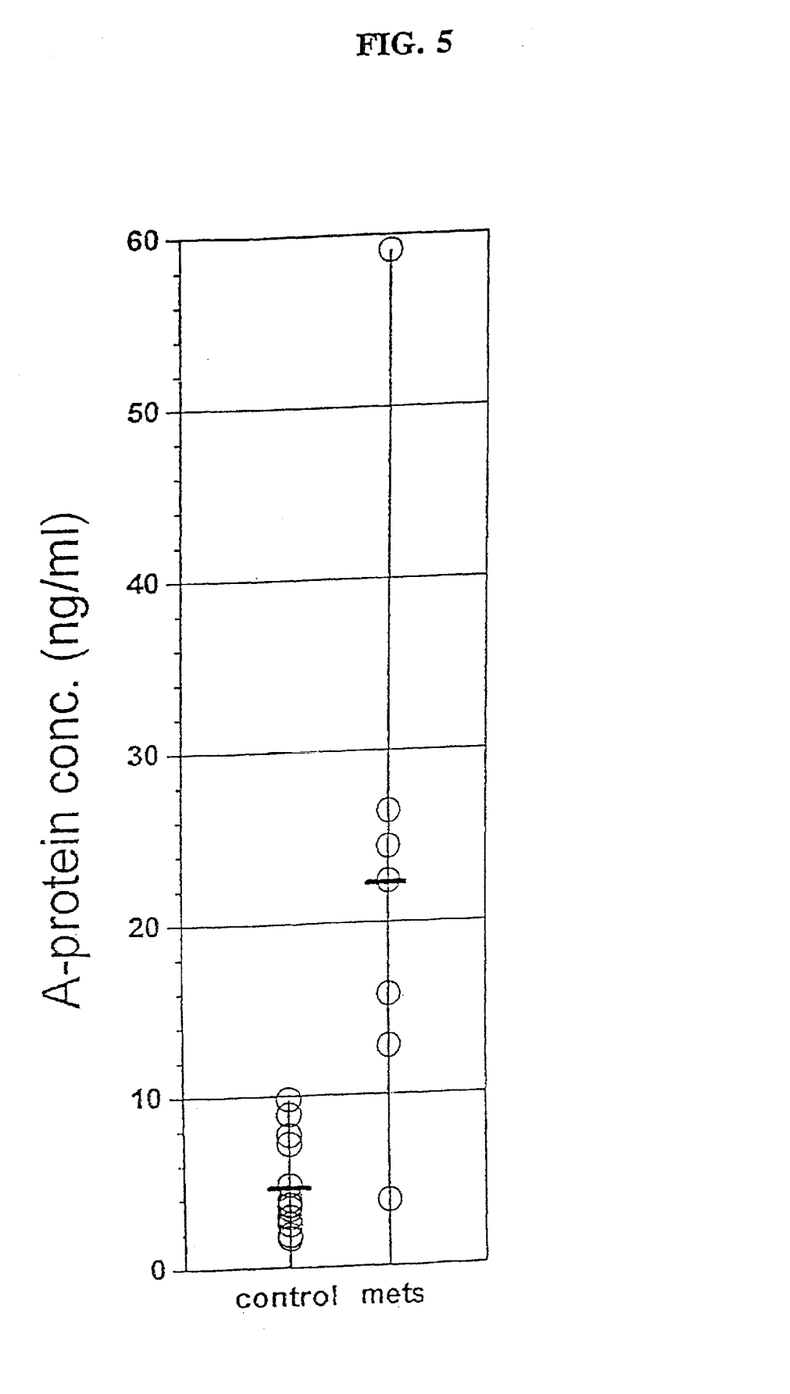
FIG. 5 is a scattergram which depicts the A-protein concentration in blood for control individuals and for individuals that have been diagnosed as having metastatic breast cancer.

In contrast to the effect of adenosine nucleotides on the binding of Gpp(NH)p, they had negligible effects on the hydrolysis of GTP by A-protein. However, at micromolar concentrations, GTPγS was found to significantly inhibit the hydrolysis of ATP during the course of a one hour incubation (FIG. 4). GTP has a similar but less pronounced effect on ATP hydrolysis, indicating that both nucleotides compete for the same or closely related binding sites on A-protein. These results also support the finding that GTP is a more effective competitor than ATP for A-protein binding.

D. Protein Assays

Protein concentrations were determined according to Bradford (*Anal. Biochem.*, 72:248 (1976)), using the Bio-Rad Microassay (Coomassie Brilliant Blue G-250). Bovine serum albumin was used as a standard.

On the basis of protein assays performed on the purified species, the complement of $A_m$ relative to $A_s$ ($A_m/A_s$) is 0.47. The ratio of the amounts of the separated soluble species recovered from high pressure columns (as estimated by optical density at 280 nm) and slab gels (as estimated by densitometry) is approximately unity. This indicates that all forms of A-protein are extracted in equivalent amounts from rods if the two soluble forms are the products of separate genes. If not, the membrane-bound form would thus be present at half the concentration of the soluble.

E. Assay for A-Protein

The antibodies of this invention produced against A-protein were used to create an assay for the detection of that antigen in the serum of humans. The procedure employs an enzyme-linked immunosorbent assay (ELISA). A specific version of this assay is presented below in Example 8.

The type of ELISA being used in this context was of the "sandwich" variety. This assay requires two different antibodies that are specific for A-protein, where each antibody recognizes and binds to different epitopes on the protein. One of the antibodies serves as the "capture" agent and was used unmodified to coat the bottom of a chamber in a standard 96-well microtiter plate. The unused portion of this antibody was then removed from the well and a blocking agent (1% bovine serum albumin (BSA)) was then placed in the chamber to block non-specific binding sites. Serum from the propositus was then incubated in the prepared well for from 1 to 12 hours, and then removed. The well was washed with a detergent solution, and the second antibody in solution was added to the well. The second antibody used in this procedure is physically linked to a labeling substance such as an enzyme; for example, the enzyme could be horseradish peroxidase (HRP). Following this incubation, the second antibody was removed and the well was washed once more. The final step consisted of adding an appropriate calorimetric substrate.

The specificities of these antibodies for different epitopes in A-protein were predetermined by performing the ELISA using various combinations of capture and conjugated enzymes with purified antigen (A-protein) to determine possible overlap of recognition sites.

The amount of color development was directly proportional to the amount of enzyme-linked antibody bound in the well, which is proportional to the amount of antigen bound in the well by the "capture" antibody. The results were quantitated by a spectophotometric determination of the amount of color produced over a predetermined period of time (typically 30 to 120 minutes). The ELISA described above has been used to test human serum from normal healthy volunteers, and cancer patients, for the presence of the A-protein antigen. The normal population was used to determine the threshold of positivity in this assay. The sensitivity of the assay extends at least to the single ng/ml range as determined by the construction of standard sensitivity curves using known amounts of purified antigen.

The patient population tested in preliminary use of this assay yielded the following qualitative results. A positive reaction in the test was obtained from patients diagnosed with lung, lymphoma, stomach, colon, rectal, and breast cancer when compared to normal subjects.

EXAMPLE 5

Preparation of Rabbit Polyclonal Antibodies that are Immunoreactive with the Carboxyl Terminal Region of A-Protein The following procedures were used to generate rabbit polyclonal antibodies that were immunoreactive with the carboxyl terminal portion of A-protein.

In one procedure, the carboxyl terminus 14 amino acid of the published sequence, QFEPQKVKEKMKNA (SEQ ID NO: 3), of human A-protein was synthesized. A mixture of this synthetic peptide in Freunds adjuvant was injected subcutaneously at 3–4 separate sites in each rabbit. The amount of synthesized peptide in each injection was 50 μg. Two weeks later, boost injections of 50 μg synthesized peptide in Freunds adjuvant were given at 3–4 separate sites in each of the previously inoculated animals. After two weeks, test bleeds were made to assess blood antibody titers with the synthesized peptide. Further boost injections were made as needed to maintain adequate blood antibody titers. Sera from rabbits with adequate blood antibody titers were collected and the desired antibodies were obtained as a purified fraction by affinity chromatography techniques using the synthesized carboxyl terminus peptide immobilized on a solid matrix. The purified antibodies were precipitated by dialysis in water and stored as a dry powder for subsequent use. These rabbit polyclonal antibodies were reactive with the peptide derived from the carboxyl terminal region of A-protein and were designated as CY2A antibodies.

In another procedure, a peptide sequence of approximately 16 amino acids at the carboxyl terminus of A-protein was synthetically produced. This peptide was then conjugated to the potent immunostimulator (adjuvant) molecule-:keyhole limpet hemacyanin (KLH). The peptide-KLH conjugate was then injected into rabbits by standard procedures used to generate antibodies. The rabbits were subsequently bled and the sera were tested and shown to be positive for the A-protein carboxyl terminus peptide used in the immunogen. These rabbit polyclonal antibodies were designated as CPDD antibodies.

EXAMPLE 6
Assay for the Presence of A-Protein in a Liquid Sample

In order to detect the presence of A-protein in a specified sample, one of the following procedures was performed:

A. Aliquots of a standard solution containing one of the monoclonal antibodies of Example 3 (the 3B9E1 antibodies) were placed in each well of a 96 well titration tray and allowed to dry so the residual antibodies adhered to the bottom substratum of each well. Aliquots of a 1% bovine serum albumin solution were added to each well for blocking purposes. Residual liquid was removed. From each sample to be tested, 50–100 µl of the sample were placed in specified wells and incubated for one hour at room temperature. The liquid portion was decanted and each well was washed with phosphate buffered saline (PBS). Aliquots of a standard solution containing the antibodies of Example 5 (the CY2A antibodies), to which horseradish peroxidase had been linked, were applied to each well and incubated for one hour at room temperature. The liquid portions were removed and each well was washed with PBS. Finally, aliquots of the horseradish peroxidase substrate, 2,2'-azino-di-[3-ethyl-benzthiazoline sulfonate (6)] diammonium salt (ABTS), were added and development was allowed to occur for one hour at 37° C. The degree of color development for each well was quantified by obtaining a spectrophotometric reading at 410 nm. These color measurements were converted to units by comparison to a calibration curve.

B. In another procedure, a biotin/streptavidin detection system was utilized. The CPDD antibody of Example 5 was first conjugated to biotin using covalent binding chemistry. An activated N-hydroxy-succinimide ester of biotin was allowed to react with purified antibody so that covalent binding of the biotin molecules to primary amines on the antibody molecule occurred. Unreacted biotin was removed by chromatography. The antibody was then titered with the immunizing antigen to find the optimal assay dilution.

In general, the procedure was performed as follows:

The biotinylated antibody was first allowed to bind to its target antigen. Simultaneously, a second antibody immobilized on a solid phase support (microtiter plate) captured the same antigen. After removal of any unbound antibody by washing, the antibody:antigen:biotinylated antibody complex was reacted with streptavidin conjugated to a reporter molecule, usually an enzyme such as horse radish peroxidase. Another wash step was performed to remove unbound streptavidin:enzyme. A substrate specific for the enzyme labeled streptavidin was then allowed to react with the remaining streptavidin:enzyme complex. The amount of substrate hydrolyzed into the chromogenic product was thus directly proportional to the amount of antigen present in the sample.

The advantage of the biotin/streptavidin detection system is that the antibody can be gently labeled with multiple biotin molecules without loss of antibody activity. The fact that more than one biotin is present on each antibody molecule allows the signal to be amplified through the subsequent binding of multiple streptavidin molecules.

Specifically, the procedure using the biotinylated antibodies was performed in the following manner:

Aliquots of a standard solution containing one of the monoclonal antibodies of Example 3 (the 3B9E1 antibodies) were placed in the individual wells of a microtiter plate. The antibodies were allowed to adsorb to the bottom and sides of each well. The residual solutions were aspirated from the wells and aliquots of a 1% bovine serum albumin solution containing 20% sucrose were added to each well for blocking purposes. Residual liquid was removed.

The subsequent reagents were initially allowed to warm to room temperature. Patient samples (EDTA plasma) were mixed and, if there was any particulate matter observed, the sample was clarified by centrifugation. A 50 µL aliquot of patient plasma and 200 µL of the biotinylated CPDD rabbit polyclonal antibody in 0.05M phosphate buffered saline at pH 7.4 with 1 mg/mL bovine serum albumin were mixed and added to the individual wells. These solutions were allowed to incubate in the wells for 2 hours. They were then aspirated and the wells were washed 3 times with aspiration.

At this point in the procedure, 200 µL of streptavidin:horse radish peroxidase enzyme conjugate were added to each well and allowed to incubate for 1 hour at ambient temperature. The wells were then washed and aspirated 3 times as above. After this step, 200 µL of tetramethylbenzidine substrate were pipetted into each well and incubated 20 minutes at ambient temperature. Then, 100 µL of stop solution (0.05N sulfuric acid) were added. Absorbance for each well was read on a dual wavelength microtiter plate spectrophotometer at 450/630 nm. The mean absorbance for each sample was computed. (If duplicates disagreed by more than 10%, the sample was repeated.) Samples with absorbance readings off scale were diluted and reassayed. The mean of each sample was divided by the mean of the negative controls to give a P/N value. Samples with a P/N greater than 2.0 were reported as positive.

To establish the baseline for the negative control value (N), 40 negative samples were initially assayed in duplicate to identify those most appropriate for establishing a cutoff between positive and negative samples. A geometric mean was then calculated by eliminating the two highest and lowest absorbance samples and recalculating the mean and standard deviation of the remaining samples. The cutoff for positivity was then arbitrarily set at 2 standard deviations above the mean for the remaining samples. Coincidentally, the mean plus 2 standard deviations was very close to 2 times the mean. Hence, some assays used a cutoff of positivity of 2.0 where the unknown sample was divided by the mean of the negative control samples to establish a so-called P/N ratio.

Subsequently, a pool of negative human serum was obtained to serve as the assay control/standard. This material had a mean absorbance essentially identical to the geometric mean of the negative samples above. Thus, this negative control was calibrated against negative sera to serve as the assay control. This assay control pool was run in duplicate for each assay and the mean absorbance calculated with the cutoff for positivity stated as 2 times the mean of the negative control.

EXAMPLE 7
Screening Procedure for Predicting Presence of Metastatic Cancer.

Blood samples from several individuals were collected. Included within the group of individuals were persons diagnosed as having metastatic breast cancer, persons from a control population with no signs of cancer, and persons that had previously been diagnosed as having had cancer but, at the time of blood sampling, were diagnosed as having their breast cancer in a state of remission.

A portion of the blood sample from each individual was used as the sample in the assay of Example 6A. The results of the assay for the blood sample from each individual is shown in Table 4.

TABLE 4

| Sample | Diagnosis | Assay Result (ng A-protein/ml blood) |
|---|---|---|
| gjs | control | 2.4 |
| afb | control | 7.6 |
| sac | control | 2.4 |
| CY 02 | NED(prostate) | 1.8 |
| CY 08 | control | 1.6 |
| 2 | control | 3.5 |
| 3 | control | 9.7 |
| 6 | control | 8.8 |
| 7 | control | 2.8 |
| 8 | control | 7.1 |
| 4 | NED | 4.7 |
| 1 | NED | 3.5 |
| 9 | NED | 3.8 |
| 5 | NED | 3.3 |
| 18 | Mets; no chemo | 15.7 |
| 49 | Mets; no chemo | 3.7 |
| 132 | Mets; no chemo | 12.7 |
| 423 | Mets; no chemo | 24.3 |
| 424 | Mets; bgnchemo | 26.4 |
| 515 | Mets; no chemo | 59.0 |
| 541 | Mets; no chemo | 22.3 |

The diagnosis labeled as NED refers to no evidence of disease recurrence. The results of this assay are also displayed in FIG. 1. The average assay result for the combination of individuals identified as controls and persons whose cancer was in a state of remission is 4.5 ng. A-protein/ml blood. The average assay result for the individuals with metastatic breast cancer is 23.4 ng A-protein/ml blood. With the exception of one individual who was diagnosed as having metastatic cancer but had an assay result within the control and NED range, all assay results could be clearly divided into two distinct groups: those individuals who had no sign of cancer and those individuals who had metastatic breast cancer. Such a demarcation is unusual. The statistical significance of these results was p<0.001 by a two-tailed t-test.

EXAMPLE 8

Screening Procedure for Predictins the Presence of Primary as Well as Metastatic Cancer In an extensive screening procedure, blood plasma samples from over eight hundred human patients were subjected to the assay protocol of Example 6B. The patient population included individuals with no cancer (controls), individuals with various stages of primary cancers, individuals with metastatic cancer and individuals with benign tumors. The screening procedure was conducted in a blinded fashion and the A-protein assay results were subsequently aligned with independent clinical diagnoses for purposes of assay verification.

The results of this screening procedure are shown in Table 5. The cancer type, cancer stage and number of individuals correctly assessed by the assay compared to the results of an independent diagnosis (sensitivity) are displayed.

TABLE 5

| Cancer Type | Assay Positives/Total # of Samples | | |
|---|---|---|---|
| Breast | 24/35 = 69% | Stage | |
| | | 1 | 1/6 |
| | | 2 | 3/4 |
| | | 4 | 1/2 |
| | | ? | 19/23 |
| Primary Liver | 17/25 = 68% | Stage | |
| | | 2 | 1/1 |
| | | 3 | 5/7 |
| | | 3b | 1/1 |
| | | 4 | 2/4 |
| | | 4a | 7/9 |
| | | 4b | 1/3 |
| Pancreas | 6/9 = 67% | Stage | |
| | | 4 | 6/8 |
| | | 4a | 0/1 |
| Prostate | 24/41 = 61% | Stage | |
| | | D2 | 0/2 |
| | | ? | 25/39 |
| Bladder | 11/19 = 58% | | |
| Lymphoma | 18/32 = 56% | Stage | |
| | | ? | 2/3 |
| | | 1 | 0/1 |
| | | 1a | 1/1 |
| | | 1b | 0/1 |
| | | 2a | 1/4 |
| | | 2B | 0/1 |
| | | 2bc | 1/1 |
| | | 2c | 1/1 |
| | | 2ca | 1/1 |
| | | 3b | 3/4 |
| | | 4 | 3/6 |
| | | 4a | 0/1 |
| | | 4B | 4/4 |
| | | 4b | 1/3 |
| Head & Neck | 9/16 = 56% | Stage | |
| | | 3 | 1/2 |
| | | 4 | 4/10 |
| | | ? | 4/4 |
| Lung | 41/91 = 45% | Stage | |
| | | 1 | 4/5 |
| | | 2 | 2/4 |
| | | 3a | 2/5 |
| | | 3b | 6/13 |
| | | 4 | 10/27 |
| | | ED | 4/6 |
| | | LD | 2/7 |
| | | ? | 11/24 |
| Colon & Rectal | 17/43 = 40% | Stage | |
| | | 2 | 0/1 |
| | | 4 | 1/3 |
| | | B1 | 2/2 |
| | | B2 | 1/4 |
| | | C2 | 2/4 |
| | | D | 3/3 |
| | | ? | 8/26 |
| Leukemia | 10/26 = 38% | | |
| Multiple Myeloma | 5/5 = 100% | Stage | |
| | | 3a | 3/3 |
| | | 3b | 2/2 |
| Endometrium | 5/5 = 100% | Stage | |
| | | 4 | 1/1 |
| | | ? | 4/4 |
| Parotid | 4/4 = 100% | | |
| Cholangio CA | 3/10 = 30% | Stage | |
| | | 3 | 1/1 |
| | | 4 | 2/8 |

TABLE 5-continued

| Cancer Type | Assay Positives/Total # of Samples | | |
|---|---|---|---|
| Kidney | 2/6 = 33% | 4a Stage | 0/1 |
|  |  | 3 | 1/2 |
|  |  | 4 | 1/2 |
|  |  | ? | 0/2 |
| Cervix | 3/4 = 75% | Stage |  |
|  |  | 4 | 1/1 |
|  |  | 4a | 1/1 |
|  |  | ? | 1/2 |
| Thyroid | 2/3 = 67% | Stage |  |
|  |  | 1 | 1/1 |
|  |  | 4 | 1/2 |
| Brain | 4/6 = 67% |  |  |
| Mouth | 2/3 = 67% |  |  |
| Uterus | 2/7 = 29% |  |  |
| Metastasis (unknown origin) | 2/7 = 29% |  |  |
| Melanoma | 2/2 = 100% | Stage |  |
|  |  | 4 | 2/2 |
| Ovary | 0/2 = 0% |  |  |
| Abdominal | 1/2 = 50% |  |  |
| Urinary | 0/2 = 0% |  |  |
| Tongue | 1/3 = 33% |  |  |
| Lip | 1/1 = 100% |  |  |
| Anal | 1/1 = 100% |  |  |
| Pelvic | 1/1 = 100% |  |  |
| Inguinal | 1/1 = 100% |  |  |
| Penile | 1/1 = 100% |  |  |
| Chest wall | 1/1 = 100% |  |  |
| Fallopian Tube | 1/1 = 100% |  |  |
| Sarcomas | 2/7 = 29% |  |  |
| POEMS | 1/1 = 100% |  |  |
| Larynx | 0/2 = 0% |  |  |
| Germ Cell | 0/1 = 0% |  |  |
| Spinal Cord | 0/1 = 0% |  |  |
| Testicular | 0/1 = 0% |  |  |
| Vulva | 0/1 = 0% |  |  |
| Spleen | 0/1 = 0% |  |  |
| Summary of All Cancers | 262/518 = 51% |  |  |

In addition, the assay was performed for normal (non-cancerous state) individuals and for persons with benign tumors. The results are shown in Table 6, where a "correct" assay result occurred (proper determination that the individual does not have cancer) when the P/N ratio for that individual was less than or equal to 2.0.

TABLE 6

| | Assay Result of Low Antigen Amount/Total No. of Samples |
|---|---|
| Normals | 174/205 = 85% |
| Benign Tumors | 70/108 = 65% |

The results of these assays demonstrate that the assay procedure has marked predictive ability to discern individuals with cancer while eliminating from consideration those individuals who do not have cancer. The cancers detected by this assay include primary as well as metastatic cancers. Cancer in various stages, including stage 1 and stage 2, are detected. In particular, breast cancer, prostate cancer, primary liver cancer, lymphoma, pancreatic cancer, lung cancer, colon cancer, bladder cancer, endometrial cancer, and multiple myeloma are readily detectable with the present assay.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of detecting the presence of cancer in an individual comprising:
   (a) obtaining a biological sample from said individual;
   (b) incubating said biological sample with at least one antibody which is immunoreactive with A-protein;
   (c) detecting immunoconjugates which form as a consequence of the incubation of step (b); and
   (d) relating the amount of immunoconjugates of step (c) to the presence of cancer, wherein cancer is present when said amount is greater than a threshold value.

2. A method of detecting the presence of a cancerous state in an individual comprising:
   (a) obtaining a liquid sample from said individual;
   (b) subjecting said liquid sample to an antibody sandwich assay wherein one of the two antibodies is immunoreactive with a peptide that has a specified sequence of approximately 16 amino acids from the A-protein amino acid sequence, and the other antibody is immunoreactive with a portion of A-protein other than said peptide with the specified approximately 16 amino acid A-protein sequence;
   (c) detecting the amount of antibody-A-protein sandwich formed in step (b); and
   (d) relating said amount to the presence of a cancerous state in said individual, wherein said cancerous state is present when said amount is greater than a threshold value.

3. The method of claim 2 wherein at least one of said two antibodies is a monoclonal antibody.

4. The method of claim 3 wherein the antibody that is immunoreactive with a portion of A-protein other than said peptide with the specified approximately 16 amino acid A-protein sequence is a monoclonal antibody.

5. The method of claim 4 wherein the antibody that is immunoreactive with a peptide that has a specified sequence of approximately 16 amino acids from the A-protein amino acid sequence is a polyclonal antibody with an attached detection label.

6. The method of claim 2 wherein the liquid of said liquid sample is blood.

7. The method of claim 6 wherein:
   (i) the antibody that is immunoreactive with a portion of A-protein other than said peptide with the specified approximately 16 amino acid A-protein sequence is a monoclonal antibody adherent to a solid surface; and
   (ii) the antibody that is immunoreactive with a peptide that has a specified sequence of approximately 16 amino acids from the A-protein amino acid sequence is a polyclonal antibody with an attached detection label.

8. The method of claim 7 wherein said attached detection label is biotin.

9. The method of claim 7 wherein said threshold value is 2.0 times the mean of the negative control value.

10. The method of claim 9 wherein said cancerous state is selected from the group consisting of breast cancer, prostate cancer, primary liver cancer, lymphoma, pancreatic cancer, lung cancer, colon cancer, bladder cancer, endometrial cancer and multiple myeloma.

11. The method of claim 7 wherein said specified sequence of approximately 16 amino acids from the A-protein amino acid sequence is either amino acids 142–158 of A-protein or the 16 amino acid carboxyl terminus of A-protein.

12. A method of detecting a cancer-diagnostic protein, whose elevated level in the bloodstream of an individual is predictive that the individual has cancer, comprising:
   (a) incubating a liquid sample from said individual with an antibody that immunoreacts with a peptide that has a specified sequence of approximately 16 amino acids from the amino acid sequence of said cancer-diagnostic protein and with an antibody that immunoreacts with a portion of said cancer-diagnostic protein other than said peptide with the specified approximately 16 amino acid cancer-diagnostic protein sequence, whereby immunocomplexes between said cancer-diagnostic protein and the two antibodies are formed; and
   (b) detecting the amount of said immunocomplexes formed in step (a).

13. The method of claim 12 wherein the liquid of said liquid sample is blood.

14. The method of claim 13 wherein said liquid sample is incubated simultaneously with both said antibodies.

15. The method of claim 14 wherein:
(i) said antibody that immunoreacts with a peptide that has a specified sequence of approximately 16 amino acids from the amino acid sequence of said cancer-diagnostic protein is a polyclonal antibody with an attached detection label; and
(ii) said antibody that immunoreacts with a portion of said cancer-diagnostic protein other than said peptide with the specified approximately 16 amino acid cancer-diagnostic protein sequence is a monoclonal antibody adherent to a solid surface.

16. The method of claim 15 wherein said attached detection label is biotin.

17. The method of claim 13 wherein said liquid sample is incubated simultaneously with the two said antibodies.

18. The method of claim 13 wherein said liquid sample is first incubated with said antibody that immunoreacts with a portion of said cancer-diagnostic protein other than said peptide with the specified approximately 16 amino acid cancer-diagnostic protein sequence and then incubated with said antibody that immunoreacts with a peptide that has a specified sequence of approximately 16 amino acids from the amino acid sequence of said cancer-diagnostic protein.

19. The method of claim 18 wherein:
(i) said antibody that immunoreacts with a portion of said cancer-diagnostic protein other than said peptide with the specified approximately 16 amino acid cancer-diagnostic protein sequence is a monoclonal antibody adherent to a solid surface; and
(ii) said antibody that immunoreacts with a peptide that has a specified sequence of approximately 16 amino acids from the amino acid sequence of said cancer-diagnostic protein is a polyclonal antibody with an attached detection label.

20. The method of claim 15 wherein said cancer-diagnostic protein is A-protein.

21. The method of claim 20 wherein an amount of said immunocomplexes greater than 2.0 times the mean of the negative control value is predictive that said individual has cancer.

22. The method of claim 20 wherein said specified sequence of approximately 16 amino acids from the amino acid sequence of said cancer-diagnostic protein is either amino acids 142–158 of said cancer-diagnostic protein or the 16 amino acid carboxyl terminus of said cancer-diagnostic protein.

23. A method of detecting the presence of metastatic cancer in an individual comprising:
(a) obtaining a biological sample from said individual;
(b) incubating said biological sample with at least one antibody which is immunoreactive with A-protein;
(c) detecting immunoconjugates which form as a consequence of the incubation of step (b); wherein an amount greater than a threshold value of said immunoconjugates detected in step c) is indicative of the presence of metastatic cancer in said individual.

24. The method of claim 23 wherein said biological sample is blood.

25. The method of claim 24 wherein cancer is breast cancer.

26. An antibody which binds to an approximately 16 amino acid sequence of A-protein to form immunoconjugates whose presence in an amount greater than a threshold value in a biological sample is predictive of the presence of cancer in the individual from whom said biological sample was obtained, wherein said sequence of A-protein is selected from the group consisting of the 14 amino acid carboxyl terminus, the 16 amino acid carboxyl terminus, the amino acid sequence 60–71, the amino acid sequence 142–158, and the amino acid sequence 158–170.

27. The antibody of claim 26 wherein said biological sample is blood.

28. A test kit for detecting the presence of cancer in an individual comprising:
(a) a first antibody that immunoreacts with a peptide that has a specified sequence of approximately 16 amino acids from the amino acid sequence of a cancer-diagnostic protein; and
(b) a second antibody that immunoreacts with a portion of said cancer-diagnostic protein other than said peptide with the specified approximately 16 amino acid cancer-diagnostic protein sequence.

29. The test kit of claim 28 wherein either said first antibody or said second antibody has an attached identifying label.

30. The test kit of claim 28 wherein at least one of said first antibody and said second antibody is a monoclonal antibody.

31. The test kit of claim 30 wherein said first antibody is a polyclonal antibody with an attached identifying label and said second antibody is a monoclonal antibody adherent to a solid surface.

32. The test kit of claim 31 wherein said attached identifying label is biotin.

33. The test kit of claim 28 wherein said cancer-diagnostic protein is A-protein.

34. The test kit of claim 33 wherein said specified sequence of approximately 16 amino acids from the amino acid sequence of said cancer-diagnostic protein is either amino acids 142–158 of said cancer-diagnostic protein or the 16 amino acid carboxyl terminus of said cancer-diagnostic protein.

* * * * *

UNITED STATES PATENT AND TRADEMARK OFFICE
CERTIFICATE OF CORRECTION

PATENT NO. : 6,187,549 B1
DATED : February 13, 2001
INVENTOR(S) : Geoffrey J. Schmidt and Kenneth L. Hoffman It is certified that error appears in the above-identified patent and that said Letters Patent is hereby corrected as shown below:

On the cover page, in the title (54), delete the word "Protein" and insert therefor -- A-Protein --, thereby correcting the title to be A-PROTEIN AS A DIAGNOSTIC OF CANCER.

Signed and Sealed this

Twenty-ninth Day of May, 2001

*Attest:*

NICHOLAS P. GODICI

*Attesting Officer*  *Acting Director of the United States Patent and Trademark Office*